(12) United States Patent  
Montgomery et al.

(10) Patent No.: US 8,604,070 B2  
(45) Date of Patent: Dec. 10, 2013

(54) USE OF INHIBITORS OF THE RENIN-ANGIOTENSIN SYSTEM

(75) Inventors: Hugh Edward Montgomery, London (GB); John Francis Martin, London (GB); Jorge Daniel Erusalimsky, London (GB)

(73) Assignee: FinVector Vision Therapies, Ltd., Oxfordshire (GB)

( * ) Notice: Subject to any disclaimer, the term of this patent is extended or adjusted under 35 U.S.C. 154(b) by 0 days.

(21) Appl. No.: 13/360,895

(22) Filed: Jan. 30, 2012

(65) Prior Publication Data

US 2012/0178784 A1 Jul. 12, 2012

Related U.S. Application Data

(60) Division of application No. 12/205,090, filed on Sep. 5, 2008, now abandoned, which is a continuation of application No. 11/441,648, filed on May 25, 2006, now Pat. No. 8,003,679, which is a continuation of application No. 10/206,659, filed on Jul. 26, 2002, now Pat. No. 7,071,183, which is a continuation of application No. 09/529,628, filed as application No. PCT/GB98/03122 on Oct. 19, 1998, now abandoned.

(60) Provisional application No. 60/067,819, filed on Dec. 5, 1997, provisional application No. 60/094,902, filed on Jul. 31, 1998.

(30) Foreign Application Priority Data

Oct. 17, 1997 (GB) .................................. 9722026.3  
May 20, 1998 (GB) .................................. 9810855.8

(51) Int. Cl.  
*A61K 31/41* (2006.01)

(52) U.S. Cl.  
USPC ...................................................... 514/381

(58) Field of Classification Search  
USPC ............................................................ 514/381  
See application file for complete search history.

(56) References Cited

U.S. PATENT DOCUMENTS 5,645,839 A * 7/1997 Chobanian et al. ........... 424/400

* cited by examiner

*Primary Examiner* — San-Ming Hui  
(74) *Attorney, Agent, or Firm* — Pharmaceutical Patent Attorneys, LLC

(57) ABSTRACT

It has been found that inhibitors of the rennin-angiotensin system are useful for the treatment or prevention of conditions associated with hypoxia or impaired metabolic function or efficiency. In particular, they may be used in connection with therapy of stroke or its recurrence, the acute treatment of myocardial infarction, and the treatment or prevention of wasting or cachexia, and are thus useful in treatment of the symptoms and signs of aging. These inhibitors may also be used to enhance function in healthy subjects.

1 Claim, 2 Drawing Sheets

USE OF INHIBITORS OF THE RENIN-ANGIOTENSIN SYSTEM

RELATED APPLICATIONS

This application is a divisional application of Ser. No. 12/205,090, filed; which is a continuation application of application Ser. No. 11/441,648, filed May 25, 2006 (now U.S. Pat. No. 8,003,679); which is a continuation application of application Ser. No. 10/206,659, filed Jul. 26, 2002 (now U.S. Pat. No. 7,071,183); which is a continuation application of application Ser. No. 09/529, 628, filed Apr. 17, 2000 (now abandoned); which is a National Stage Application of International Application No. PCT/GB98/03122, which claims the benefit of Provisional Application Ser. No. 60/067,819, filed Dec. 5, 1997 and Ser. No. 60/094,902, filed Jul. 31, 1998 and further claims priority to United Kingdom Application No. 9722026.3, filed Oct. 17, 1997 and United Kingdom Application 9810855.8, filed May 20, 1998; all of which are incorporated herein by reference in their entireties.

FIELD OF THE INVENTION

This invention relates to the use of inhibitors of the renin-angiotensin system.

BACKGROUND OF THE INVENTION

Wasting diseases may be categorised into generalised and localised wasting diseases. To deal first with generalised wasting, many disease processes can lead to aggressive generalised weight loss through either the inability to consume sufficient nutrients and energy sources, through their loss from the body (either enterally or in the form of cellular matter), or through an inability to absorb them. Other diseases are associated with marked weight loss quite out of proportion to any reduction in nutrient absorption or increase in nutrient loss. Such weight loss may have a metabolic origin. Severe cardiac failure as well as renal, hepatic and malignant disease processes are all associated with such inappropriate weight loss. Some neurological diseases, such as Parkinson's disease and syndrome are similarly related, as are conditions associated with inflammatory processes, such as severe sepsis or septic shock and autoimmune and connective tissue disorders. This weight loss may at best be disabling, and at worst associated with an increased mortality. Current treatment and preventative strategies largely focus on nutritional support.

In localised wasting, disuse of any given muscle group (for instance due to musculoskeletal or neurological injury) may lead to wasting in the affected territory. There are currently no available treatments which are routinely used to slow or limit such wasting, nor which have been shown to accelerate the reversal of such wasting with appropriate exercise or after the cessation of the initiating disease state.

Current strategies for the promotion of trainability and fitness have largely focused on alterations in training pattern. More recently, nutritional supplementation has been suggested using the manipulation of scale and nature of intake of carbohydrates, fats, vitamins and amino acids. The addition of other substrates, such as creatine derivatives, have also been used. Most such interventions are either currently unproven, or have been shown to have no or only modest influence. Endocrinological interventions have been attempted, including the use of androgens and other steroid hormones. The use of insulin or of growth hormone may also have a role. However, these treatments may be associated with an unacceptable side-effect profile and also suffer from the disadvantage that they have to be parenterally administered (usually by intramuscular injection). Pharmacological manipulations are not currently available.

The possibility of improving cardiovascular, and other organ, function is known in connection with the phenomenon of "preconditioning". The exposure of an organ—most notably the heart—to a brief period of reduced blood flow or oxygen supply has been shown to provide protection against a second more severe similar event which might otherwise prove lethal to cells or the organ itself. Much research is currently being undertaken in an effort to identify pharmacological agents which might mimic this process. None is available for routine clinical practice.

The renin-angiotensin system (RAS) and its components may be described as follows. Briefly, cells of the renal juxtaglomerular apparatus produce the aspartyl protease renin which acts on the alpha-2 globulin angiotensinogen (synthesised in the liver) to generate angiotensin I (AI). This non-pressor decapeptide is converted to angiotensin II (ATII) by contact with the peptidyldipeptidase angiotensin-converting enzyme (ACE) (reviewed in (1)). ATII stimulates the release of aldosterone, and is also a potent vasoconstrictor. The renin-angiotensin system is therefore important in the maintenance and control of blood pressure as well as the regulation of salt and water metabolism. Renin, angiotensinogen and ACE have also been identified in cardiovascular tissues including the heart (2) and blood vessels, as has mRNA for components of this system such as angiotensinogen (3-5). Receptors for angiotensin II have been found on vascular smooth muscle cells (6). Within tissues, the RAS may therefore have a local paracrine function (reviewed in (7, 8)), and the expression of the different components can be altered by pathophysiological stimuli such as sodium restriction (5). Kinetic studies suggest that much of the circulating angiotensin I and II is derived from the both renal and non-renal tissues (9-11).

ACE is a zinc metallo-protease which catalyses conversion of the inactive decapeptide ATI to the active octapeptide ATII thorough the hydrolytic cleavage of dipeptides from the carboxyl terminus His-Leu dipeptide. It also catalyses inactivation of bradykinin (a patent vasodilator) by two sequential dipeptide hydrolytic steps; in this context, ACE is also known as kininase II.

The presence of renin-angiotensin system (RAS) components in many animal species (such as locusts and elasmobranchs) suggests that they must have some other role than that of a conventional circulating RAS. This function must be fundamental and important in order to have been phylogenetically conserved over many millions of years. In fact, complete renin-angiotensin systems are now thought to exist within many human (and animal) tissues: physiologically-responsive gene expression of RAS components within these tissues, local generation of ATII, the presence of ATII receptors and the demonstration that these receptors are physiologically active have all been shown. Thus, angiotensinogen messenger RNA (mRNA) is identified in renal, neural and vascular tissues, and local synthesis may strongly influence its concentration in interstitial fluid (10). Renin mRNA (12) and product (13) is found in cultured mammalian vascular smooth muscle cells and throughout the vessel wall (13), and in rat ileum, brain, adrenal, spleen, lung, thymus and ovaries. Liver renin gene expression is physiologically responsive, being increased 3-fold by sodium deprivation or captopril administration (14).

Non-renin angiotensinogenases may also exist in tissues. A neutral aspartyl protease with renin-like activity has been demonstrated in canine brain (15, 16). Some (e.g. tonin, elastase, cathepsin G and tissue plasminogen activator) can cleave ATII directly from angiotensinogen (16).

ACE expression occurs at high level in vascular endothelium, but also in the small intestinal epithelium, the epididyrnis (17) and brain (15). Tissue-specific/age-related ACE gene transcription occurs in renal tissue (where there is very high proximal tubular epithelial expression), and in cardiovascular, hepatic and pulmonary tissues (18).

Such local systems may be paracrine in nature: receptors for ATII are classically described as existing on cell surfaces, allowing transduction of the effects of endocrine and paracrine ATII. However, true autocrine systems (intracellular production and actions) may also exist. ATII receptors may also exist on the cell nuclei. Specific binding sites for ATII exist on cellular chromatin which may regulate gene transcription (19, 20).

There are many marketed or investigation-stage agents which inhibit RAS activity, and many of them fall into two broad classes: the inhibitors of angiotensin-converting enzyme, whose approved names generally end in "-pril" or in the case of active metabolites "-prilat", and antagonists at angiotensin receptors (more specifically, currently, the $AT_1$ receptor), whose approved names generally end in "-sartan". Also potentially of increasing importance may be a class of drugs known as neutral endopeptidase inhibitors, some of which will also have an ACE-inhibitory effect or the potential to reduce RAS activity.

Brink et al. (21) suggested that angiotensin II may have a metabolic effect in rats (in vivo experimental work) which is independent of its effects on blood pressure.

There is evidence that angiotensinogen gene expression is differentially modulated in fat tissue in obese rats when compared to their equivalent lean strain (22). ACE inhibition increases rabbit hind leg oxygen consumption at high work loads, but not at lower workloads (23).

ACE inhibitor (ACEI) increases insulin-dependent glucose uptake into the skeletal muscle of an obese rat strain which exhibits relative insulin-resistance (24), and this may be kinin-dependent (25). Glucose transporter levels were elevated in this study, as they were sustained by $AT_1$ receptor antagonism in the diabetic rat heart (26).

ATII increases rat hind limb $O_2$ usage and twitch tension (27). This paper concludes that the effects might have been due to effects on blood flow or neurotransmission and not to a direct metabolic effect.

In heart failure in dogs, fatigue-resistant fibres are conserved by ACE inhibitor therapy (28). In rats, capillary density is maintained, and collagen volume reduced (29, 30).

Kininases (such as ACE) have been shown to exist in the cell membranes of human skeletal muscle (31). Thus, skeletal muscle RAS may exist (32).

In vitro, ACE inhibitors cause an increase in myocardial oxygen utilisation. Whether this was due to increased or reduced efficiency was unclear (33). This work related to myocardial muscle extracts. This effect may be due to reduced kinin breakdown, and thus increased kinin levels, despite the fact that angiotensin II may modulate (and increase) kinin release (34).

Other publications suggest an effect of ACE inhibitors or of angiotensin II on muscle performance or metabolism, but all of these have concluded that the effects are mediated by alterations in nutritive blood flow (35, 36).

In human forearm, kinins increase blood flow and glucose uptake, although again a direct effect of RAS, or an effect on performance, was not detailed (37).

Losartan (an $AT_1$ antagonist) improves insulin sensitivity in human skeletal muscle (38).

Other publications suggest no beneficial effect of ACE inhibition, amongst those with heart failure in muscle energy balance (39). ACE inhibition did not alter perceived work or maximal work capacity of 20 students on a bicycle ergometer (40).

SUMMARY OF THE INVENTION

It has now been found that renin-angiotensin systems are implicated in the regulation of cellular metabolic efficiency, in the mechanical efficiency of tissue systems such as cardiac and skeletal muscle, and in the regulation of growth of cardiac and skeletal muscle. This observation leads to the possibility of down-regulating the activity of this system (thus reducing the action of the substance angiotensin II and increasing the activity of kinins) so as to enhance metabolic efficiency and enhance mechanical performance of tissues. Such enhancement allows improved management of diseases involving wasting (including severe inflammatory conditions, severe heart failure and malignant states), the ability to offer relative protection to tissues from periods of reduced oxygen supply and the ability to enhance human and animal physical performance. In summary, the present invention is based on the discovery of a previously unknown effect of RAS-inhibitors, i.e. for the promotion of metabolic function or efficiency.

Improvement in metabolic function or efficiency may be seen as: improvement of cellular function and survival in the presence of low oxygen supply relative to demand; enhancement of mechanical performance of human skeletal and cardiac muscle; and/or enhancement of nutritional status.

The invention therefore finds application in:
a. the treatment and prevention of wasting disorders such as cachexia in malignant disease, acute and chronic sepsis, chronic hepatic diseases, end-stage renal disease, AIDS and immune system disorders, and cardiac failure;
b. the promotion of cardiovascular fitness, human physical performance, and physical endurance and the improvement of the ability of these parameters to respond to physical training, as well as helping sustain these parameters (this applies to the physical training of individuals, as well as to the training of muscles for specifically therapeutic purposes such as cardiomyoplasty); and/or
c. influencing the alteration in body composition and/or morphology associated with exercise, by altering muscle and fat content.

There is a need for new methodologies in these areas. This need applies particularly to humans, but where appropriate may also apply to the treatment of other mammals.

In particular, the present invention utilises the availability of effective agents with low toxicity and side-effect profiles, and which may be administered enterally or parenterally, to allow manipulation of human physical performance. This may fall into four main areas:

a. sporting applications, including improved sporting prowess and more rapid recovery of function and performance after injury;
b. military and social situations where enhanced physical performance may be paramount, e.g. those encountered by military personnel, fire-fighters and police forces;
c. the enhancement of performance in environments where oxygen supply is diminished, such as at altitude, and in disease states associated with low tissue oxygen delivery; and
d. the enhancement of respiratory muscle training and recovery of respiratory muscle function after a protracted period of mechanical ventilation, thus aiding weaning from mechanical ventilation on intensive care units.

Improved physical fitness would allow improved ability to complete tasks. Cardiovascular and cardiorespiratory fitness is also associated with reduction in mortality and morbidity rates from cardiovascular causes.

Agents may be used, in accordance with the invention, to limit tissue damage (e.g. cerebral or cardiac) in the event of a clinical event of the type seen in connection with preconditioning, when applied to individuals at risk of such events (e.g. those at risk of stroke or heart attack, or those about to undergo a procedure associated with low oxygen delivery, such as coronary angioplasty or cardio-pulmonary bypass). This effect might also provide protection to cells and tissues, and ultimately to life, in those who are at risk of, or who suffer, exposure to global (rather than tissue-specific) low oxygen delivery. Such individuals would include mountaineers at high altitude (the function of whose organs, including the brain and heart, would be improved, thereby preventing damage to them) and those with severe circulatory failure. Others with severe hypoxaemia who might also benefit include those with severe lung disease or circulatory derangements which are associated with profound hypoxaemia. Such conditions include infections such as pneumonia, adult respiratory distress syndrome, pulmonary embolic disease, pulmonary fibrosis, Eisenmenger's syndrome and cardiac left-to-right shunts.

Altering the metabolic efficiency of tissues, as well as the mechanical efficiency of muscle function (and hence the metabolic demands of the body), would lead to alterations in body fat utilisation. Further, manipulation of muscle mechanical efficiency may also alter muscle growth. In this way, improving metabolic efficiency may alter the response of body morphology to a period of exercise training and to altered dietary intake. Such an improvement would also modify a system which may have direct trophic effects on muscle, and might therefore alter skeletal muscle growth by a second mechanism. An improvement in metabolic efficiency would also limit cardiac growth in response to severe exercise or pressure burden.

Particular areas of interest, within the context of this invention, are the treatment or prevention of the effects of ischaemia, including global ischaemia, renal and intestinal ischaemia, stroke, unstable angina, stable angina, myocardial infarction (immediately after occurrence), peripheral vascular disease, cerebral palsy, chronic or acute respiratory diseases (which may be associated with hypoxaemia), including respiratory distress syndrome, interstitial lung disease, hypoxaemia, car pulmonale, disorders involving a shunt between the pulmonary and systemic circulations, conditions causing hypoperfusion of vital organs, cardiac arrest, septic states including meningococcal septicaemia, sickle cell anaemia, CO poisoning and resuscitation from drowning. A use of interest and value is the prevention of hypoxia during birth, by administration to the mother, thereby potentially reducing the chance of the child being brain-damaged; this is particularly relevant if it is anticipated that the birth will be difficult.

Evidence presented below indicates that the effect of RAS inhibitors on mitchondrial function is consistent with the theory presented herein. It also explains the utility of such agents in cardiac problems, but broadens the scope of their utility, e.g. to non-cardiac uses, in brain, liver, kidney etc, and in skeletal muscle; Cells are able to function effectively under conditions of reduced oxygen availability, and/or to utilise oxygen more efficiently. Thus, in connection with the treatment or prevention of stroke or its recurrence, the penumbra of oxygen-starved cells around a clot or hemorrhage can function more efficiently. The stroke may be thrombotic or hemorrhagic, cerebrovascular or accident in origin. Further, a RAS-inhibitor may be of benefit in the transport or survival of transplanted organs.

The invention has utility in therapy in general, in the treatment and also the prevention of adverse conditions. It has utility in treating symptoms associated with such conditions, e.g. wasting. It also has utility in enhancing performance where the subject would normally be regarded as healthy, i.e. without reference to any particular adverse condition. One particular area of interest is ageing, i.e. where the subject may or may not be ill, but where use of the invention can positively affect the well-being of the subject, Inhibitors of RAS have been given to subjects having raised blood pressure, and it may be that this will have provided effects associated with the present invention. An aspect of the present invention is the realisation that such agents are useful when the subject has normal blood pressure, and that the effects are independent of any effect on blood pressure. The invention is of value where undue reduction in blood pressure does not occur, or is not a problem.

DESCRIPTION OF THE INVENTION

Figure 1:
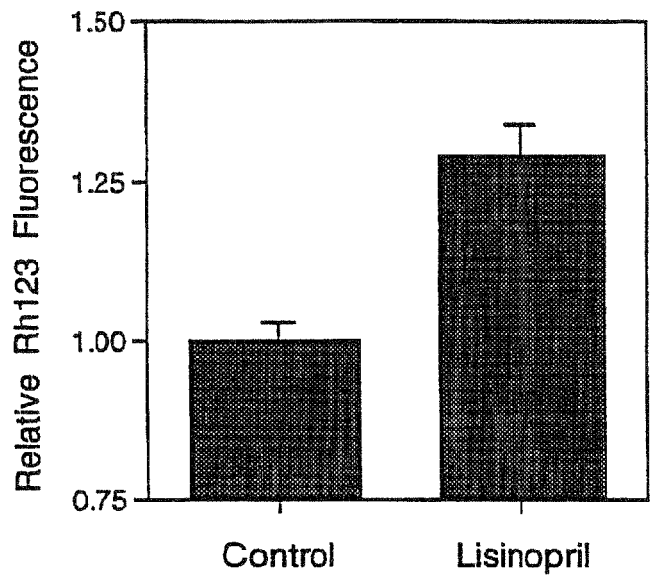
FIG. 1 shows the pre-treatment of cardiomycocytes with 1 µM lisinopril for 36 hours caused an increase in Rh123 fluorescence of about 30%, indicating that ACE inhibition induced an increase in $\Delta\Psi_m$.

The invention may be utilised to affect any RAS. Amongst other tissues, local tissue renin-angiotensin systems have been suggested in the brain, blood vessel wall, heart, intestine, liver and kidney.

Having described the various components of the RAS above, it will be apparent that the system can be inhibited at various points. In principle, it is expected that any sufficiently non-toxic compound which is bioavailable and active to inhibit the RAS system at any suitable point can be used in the invention. This invention contemplates the administration of all such agents (either singly or in combination with each other and/or with other classes of pharmacological agents), and also of pro-drugs which are converted in vivo to an active agent which inhibits RAS activity. Note that RAS inhibition need not be total inhibition; rather, sufficient inhibition to be beneficial in the invention is all that is required. In practice, it is preferred at the present state of knowledge to use in the practice of the invention any of the known RAS inhibitors which are either on the market or under investigation for their antihypertensive effects.

Many inhibitors of the renin-angiotensin system are licensed or under investigation for use in humans in the United Kingdom and are compounds whose use is preferred in the practice of the invention. They include the ACE-inhibitors Quinapril, Captopril, Lisinopril, Perindopril, Trandolapril, Enalapril, Moexipril, Fosinopril, Ramipril, Cilazapril, Imidapril, Spirapril, Temocapril, Benazepril, Alacepril, Ceronapril, Cilazapril, Deiapril, Enalaprilat and Moveltipril. Suitable angiotensin II-inhibitors include Losartan, Valsartan, Irbesartan, Candesartan, Eprosartan, Tasosartan and Telmisartan.

The specific compounds listed may be useful in accordance with the invention in their free form, for example as the free acid or base as the case may be, and they may be useful as acid addition salts, esters, N-oxides or other derivatives as appropriate. The use of suitable pro-drugs (whether themselves active or inactive) and the use of active metabolites of RAS inhibitors are also within the scope of the invention. For example, alacepril is a pro-drug for captopril, and enalaprilat is an active metabolite of enalapril.

Although ACE inhibitors and angiotensin II-receptor antagonists are presently the most widely developed classes of drugs suitable for use in the present invention, the invention is by no means limited to their use. Other inhibitors of the RAS system include resin inhibitors and neutral endopeptidase inhibitors: ACE inhibitors may work through both a reduction in ATII formation and through a reduction in kinin metabolism. Other agents may also inhibit kinin degradation, and as such have similarly beneficial effects. These classes of drugs include inhibitors of neutral endopeptidases, some of which also of ACE-inhibitory properties. The invention thus contemplates the use of all kininase-inhibitors and kinin receptor antagonists (such as bradykinin).

In many circumstances, it may be that a combination of the tissue/metabolic effects of such antagonists to the RAS with their systemic effects (e.g. reduced blood pressure, reduced cardiac preload or afterload and vasodilatation) and other combined effects (e.g. ventricular remodelling) may be of value. Such circumstances might be in the treatment of patients with hypertension, peripheral vascular disease, cardiac failure or cardiac hypertrophy.

In normotensive subjects, or in hypotensive individuals (either through the effect of other drugs, through natural phenotype, or through disease states such as sepsis or septic shock) any further reduction in blood pressure or other systemic effects of RAS antagonists might be disadvantageous. Under such circumstances, the use of lipophilic, or even highly lip ophilic, agents may have advantages in enabling tissue-RAS inhibition to be achieved without effect on systemic blood pressure. That this can be done in animals has been shown by many groups. Indeed, even in a profoundly hypertensive animal model, 5 µg/kg/day of ramipril administered to rats had no effect on systolic blood pressure. This technique of using very low doses of a lipophilic ACE inhibitor has also been applied to humans: a low dose of ramipril could produce significant biological effect without any recordable effect on systemic blood pressure (41).

The invention contemplates the use of compounds which are essentially non-lipophilic, or only moderately lipophilic, but which have been rendered more lipophilic either chemically, such as by appropriate derivatisation, or physically, such as by formulation with lipophilic carriers or delivery systems.

Compounds having activities as described above are useful, in accordance with the invention, for promoting metabolic function or efficiency and hence improved biochemical and mechanical function. This may be achieved through a variety of mechanisms (above) which may include:
improved blood supply (and hence substrate supply);
increased substrate uptake (e.g. of glucose or oxygen); and/or improved cellular efficiency in the use of these substrates (e.g. achieving the same mechanical or biochemical work for the use of less oxygen or metabolic substrates).

The first two examples may be regarded as improved metabolic function, and the third may be regarded as improved metabolic efficiency.

In particular, it is envisaged that the invention will be useful in treating those conditions, and addressing those situations, in relation to which it was discussed above that there was currently an unmet need. These include treating wasting diseases, promoting trainability and fitness, and altering body composition and/or morphology. Generally speaking, a RAS inhibitor may be administered at any effective but tolerated dose, and the optimum dose and regimen can be established without undue difficulty by essentially conventional trial work. Some general guidance follows, but ultimately the appropriate dosage and regimen of each drug for the various conditions within the ambit of the invention will be within the control of the clinician or physician. In general, compounds useful in the invention may be given by oral therapy (by mouth) or enteric therapy (administration through nasogastric, nasoenteric or other enteric feeding tubes) or parenterally, such as intravenously, for example by the addition of compound(s) to bags of parenteral nutrition.

Generalised Wasting:

It has been discussed that many disease processes, including severe cardiac, renal, hepatic and malignant disease, respiratory disease, AIDS, and chronic or acute inflammatory processes such as severe sepsis (or septic shock) and autoimmune and connective tissue disorders, can lead to a generalised weight loss through a metabolic mechanism. The present invention enables the prevention or treatment of such conditions with the RAS inhibiting agents as described above. It is anticipated that low doses of such agents (e.g. 1.25 mg of ramipril) may be effective. In principle, however, a similar strategy to that used in the treatment of heart failure would seem most likely to be used, namely a steady increase in dosage to a maximum tolerated. The major limiting factors in treatment may be:

a. The development of cough in some individuals treated with an ACE inhibitor, although switch to another agent or class of agent might be possible; and/or b. A significant fall in blood pressure. At doses of 2.5 mg ramipril (or equivalent of other agents), a first-dose fall in blood pressure occurs with the same frequency as is seen with placebo in trials of treatment of acute myocardial infarction, suggesting that in many this sort of dose would be safe.

Appropriate doses for critically-vasodilated patients (such as those with septic shock) would be established following appropriate protocols known to those skilled in the art and/or by titration to an individual patient.

Localised Wasting:

Dosage of the RAS inhibitor may be at the maximum tolerated dose, as in the published range for each agent for use in treating heart failure or hypertension. Low doses (such as 1.25 mg ramipril) may allow benefit without any significant hypotensive effect, as discussed above.

Preconditioning:

A suitable preventative strategy would involve giving those at risk of organ ischaemia (e.g. those with significant risk of myocardial infarction or stroke) a regular dose of the agents described. Those with known poor cardiac, skeletal muscle (e.g. claudicants) or cerebral flow might also benefit from treatment, through enhancing metabolic efficiency, and providing cellular protection to critically-ischaemic cells until such time as revascularisation might be considered. Dosage of the agent classes at the maximum tolerated dose, as in the published range for each agent for use in treating heart failure or hypertension. Low doses (such as 1.25 mg ramipril) may allow benefit without any significant hypotensive effect, as discussed above. It may be possible to use parenteral formulations to provide protection to those who have just suffered such an ischaemic event or to those about to undergo a procedure leading to ischaemia, such as angioplasty or cardiac bypass.

Promotion of Trainability and Fitness:

Dosage of a RAS inhibitor may be given at the maximum tolerated dose, as in the published range for each agent for use in treating heart failure or hypertension. Low doses (such as 1.25 mg ramipril) may allow benefit without any significant hypotensive effect, as discussed above. Administration of a RAS inhibitor to those with peripheral vascular disease might be expected to improve exercise endurance and possibly limb viability through a combination of the mechanisms contemplated herein.

Alteration in Body Composition and/or Morphology:

Dosage of a RAS inhibitor may be given at the maximum tolerated dose, as in the published range for each agent for use in treating heart failure or hypertension. Low doses (such as 1.25 mg ramipril) may allow benefit without any significant hypotensive effect, as discussed above.

As far as formulation and administration are concerned, it is expected that the various drugs useful in the invention could be administered in the same formulations as currently exist. New formulations might be developed with the express intent of being able to exert a predominantly tissue-effect without significant systemic hypotensive effects, in the same way as has been described for low-dose ramipril, or for local tissue delivery or for intravenous or intra-arterial administration. Currently, there has been an emphasis on the oral administration of most of these agents. However, formulations to allow systemic parenteral administration may enhance the ability to treat the critically ill, or those undergoing interventions leading to vascular occlusion or low blood flow rates as indicated above. Additionally, new formulations (for example, for local delivery, as already mentioned) may become available.

Administration of the active agent may be by any suitable route. As is conventional for ACE inhibitors at least oral administration may be preferred, especially for the purposes of achieving a prophylactic or preventative effect. In certain circumstances, especially when a more immediate effect is required, intravenous administration may be preferred; for example, a subject who has just experienced an infarction may be given the active agent intravenously, not for the purpose of remodelling but to alleviate local oxygen demand and thereby facilitate treatment. Suitable formulations for intravenous administration will be evident to those skilled in the art.

In the above discussion, indicative doses have been given, by way of example only, as optimal doses may be established experimentally and/or clinically. It should be noted that useful doses in accordance with the invention may be below optimal anti-hypertensive doses or even below effective anti-hypertensive doses.

The optimum frequency of dosage and duration of treatment may also be established experimentally and/or clinically. Again by way of example, oral ramipril may be given once daily for an appropriate period of time. Frequencies of dosage for other compounds useful in the invention will vary, and will depend on, among other things, the pharmacokinetics of the compound in question.

The invention enables the provision of a method of promoting metabolic function or efficiency, the method comprising administering to a subject an inhibitor of the renin-angiotensin system. The inhibitor will generally be administered in an amount which is non-toxic or only acceptably toxic but which is effective to promote metabolic function or efficiency (or of course both). The subject will generally be human, but non-human animals may also benefit from the invention. Promotion of metabolic function or efficiency may be undertaken, for example, for therapeutic, prophylactic, social, military, recreational or other purposes. Preferred features of such a method of treatment are as described above.

Other aspects of the invention include:
 a method, which may be a non-therapeutic method, of promoting metabolic trainability or fitness in a healthy subject, the method comprising administering to the subject an inhibitor of the renin-angiotensin system; and
 a method, which also may be a non-therapeutic method, of altering body composition and/or morphology in a healthy subject, the method comprising administering to the subject an inhibitor of the renin-angiotensin system.

By way of illustration of circumstances in which this invention may be used, mountaineers may take ramipril at low dose (1.25-2.5 mg) for 4 weeks prior to their departure whilst training, so as to improve their trainability, recognise any side effects prior to departure, and to load their tissues with the drug. They continue to take the drug whilst on their expedition.

Another example is of an elderly, injured patient on a ventilator, who may be given a test dose of a short-acting ACE inhibitor (captopril), and side-effects (such as a decline in renal function or fall in blood pressure) watched for. The dose of ACE-inhibitor (given nasogastrically) is then increased to a maximal tolerated dose (such as 20 mg bd or enalapril, or 10 mg od ramipril). It is intended that this intervention will slow the anticipated muscle wasting (both generalised systemic, and local wasting from disuse atrophy).

A patient may be treated post-surgery, in the same way. Respiratory muscles are 'trained' by steady reduction in mechanical ventilatory support, and this training is enhanced by the therapeutic use of the ACE inhibitor.

A similar regime may be suitable for the treatment of a patient with low systemic oxygen levels due to severe lung injury from Adult Respiratory Distress Syndrome associated with a systemic inflammatory response syndrome, or severe smoking-related lung disease. It may also be used for a patient due to undergo coronary angioplasty, e.g. ramipril for 4 weeks prior to the procedure, for a patient who has suffered a coronary occlusion, and is considered at risk of further events, or who has peripheral vascular disease. Further, it may be used to manage a patient who has suffered a femoral arterial occlusion and undergone angiography; an infusion of thrombolytic agent is administered into the femoral artery directly, along with an intraarterial ACE inhibitor at the same site, to improve muscle survivability as reperfusion occurs. Another example of a suitable subject for treatment is overweight, and who finds it hard to exercise and lose weight; an ACE inhibitor may be given, in association with an intensive exercise training programme. Yet another suitable patient has smoked heavily throughout his life and suffers intermittent claudication at a distance of only 150 yards.

The invention may also be used in the treatment of subjects exhibiting severe cachexia, as has been observed in cases of TB, HIV, pleural effusion, meningitis, hepatitis, perferated stomach ulcer, liver cirrhosis, cellulitis, hepatoma, sickle cell anemia, appendicitis, sinusitis, dysphagia, abcess, pneumonia, chronic diarrhoea, encephalopathy and bone fracture.

As will also be apparent from the present disclosure, the invention includes within its scope various screening methods, including a method of diagnosing or screening an individual for an inherited predisposition to promotability of metabolic function or efficiency in a subject, the method comprising analysing detecting in the individual an allele of the ACE gene (DCP1) on chromosome 17q23.

The invention therefore encompasses each of:
A method of screening an individual for response to treatment or prevention of wasting;
A method of screening an individual for response to cardiac preconditioning;
A method of screening an individual for response to promoting trainability and fitness; and
A method of screening an individual for response to altering body composition and/or morphology;
wherein, in each case, the method comprising analysing detecting in the individual an allele of the ACE gene (DCP1) on chromosome 17q23.

In particular, such methods may comprise determining the presence (Insertion, I) or absence (Deletion, D) of a 287 base pair alu repeat sequence in intron 16. The methods may be carried out in vitro if appropriate.

ACE gene I/D genotype may be determined in a number of ways. Most currently rely upon polymerase chain reaction amplification of genomic DNA which may be derived from a number of sources. Most commonly, blood or mouthwash are used. Different primers allow specific amplification of the D of I alleles, and the corresponding fragments are then separated, usually by electrophoresis. One example of a suitable technique is disclosed in Montgomery et al., *Circulation* 96(3) 741-747 (1997), published 5 Aug. 1997.

By way of further elaboration, the I/D polymorphism may be identified by polymerase chain reaction amplification (PCR) and subsequent electrophoretic separation of fragments. Two PCR methods in particular may be used. The first-reported method of PCR amplification used two primers, has since been used in the majority of the published studies, e.g. as described by Cambien et al, *Nature* 359 641-644 (1992). It has since become clear that this system is prone to systematic bias in that the shorter (deletion) fragment is preferentially amplified at the expense of the larger insertion (I) allele. This causes misclassification of a small proportion (5-15%) of heterozygotes as being D homozygotes (Shanmugam et al, *PCR Methods Appl.* 3 120-121 (1993)). Such misclassification may be prevented by specific alterations in the PCR conditions (such as the addition of a denaturing agent such as desmethylsulphoxide, which increases the stringency of the reaction), or by the use of an insertion allele-specific third primer as described by Evans (Evans et al, *Q. J. Med* 87 211-214 (1994)).

A 3-primer PCR system, with primers as described by Evans (Evans et al, loc cit. 1994) may have a modified protocol as subsequently described: Two priming oligonucleotides flank the insertion sequence in intron 16 and a third oligonucleotide is specifically within the insertion sequence. This method yields shorter allele fragments. This, together with I-allele-specific amplification, eliminates the mistyping of heterozygotes as DD homozygotes. We used primer ratios corresponding to the 50 pmol ACE1 (5' or left hand oligo) and 3 (3' or right hand oligo) and 15 pmol ACE2 (insertion specific oligo) used by Evans et al in a 500 reaction, giving amplification products of 84 bp for allele ACE D and 65 bp for allele ACE I. Our amplification conditions were as follows: 1 cycle 95° C. 5 min; 40 cycles 95° C. 1 min, 50° C. 1 min, 72° C. 5 min, 200 PCR reactions contained 50 mM KCI, 10 mM Tris HCl pH 8.3, 1.5 mM $MgCl_2$, 0.01 mg/ml gelatin, 200 µM each dNTP, 0.2 units Taq polymerase (Gibco BRL, Paisley, UK) and 8 pmol of primers ACE1 and ACE3, outside the insertion (Alu) sequence, and 2.4 pmol of primer ACE2, inside the insertion sequence. Reactions were overlaid with 20111 mineral oil. All 96 wells were always filled with reagents (mix or dummy reagents) to ensure constant thermal mass on the block. Amplification products were visualised using electrophoresis on 7.5% polyacrylamide gels. The accuracy of our genotyping was confirmed under conditions previously reported (O'Dell, Humphries et al, *Br. Heart* 73 368-371 (1995)), such that replica PCRs set up using only the primer pair ACE I and ACE3, both at 8 pmol per 20 PCR reaction, always confirmed the presence of the D allele.

DNA fragments were separated using agarose gel electrophoresis (in the case of the 2-primer system), and electrophoresis on an 8.4% polyacrylamide gel (in the case of the 3-primer system). Fragments were identified by the incorporation of ethidium bromide into the gels, and viewing under ultraviolet light.

Preferred features of each aspect of the invention are as for each other aspect mutatis mutandis.

Large interindividual differences in plasma ACE levels exist, but levels are similar within families (42), suggesting a strong genetic influence in the control of ACE levels. The human ACE gene (DCP1) is found on chromosome 17q23 (43) and contains a restriction fragment length polymorphism (44) consisting of the presence (Insertion, I) or absence (Deletion, D) of a 287 base pair alu repeat sequence (45) in intron 16 (46). D allele frequency is approximately 0.57-0.59 (43, 45).

This I/D polymorphism has been shown to influence circulating ACE levels. Amongst 80 healthy Caucasians, the polymorphism accounted for 47% of the variance in plasma ACE, although considerable overlap existed between groups (44). Tissue ACE levels might be similarly influenced. T-cells express ACE. The facts that most of the ACE activity is microsomal, and that B-cells lack ACE mRNA expression while monocyte ACE levels are 28-fold lower, support the conclusion that T-cell ACE activity is due to cellular synthesis not passive adsorption from the circulation. ACE activity in those of DD genotype is 75% and 39% higher in plasma and T-lymphocytes, respectively, than in those of II genotype (47). Local ATII generation in human internal mammary artery may also be increased in those of DD genotype (48). Cardiac ACE activity may be similarly influenced (49). However, there is no evidence of an association of ACE genotype with circulating ATIL levels (50). These data suggest an influence of the I/D polymorphism on tissue and plasma ACE activity. Increasing D-allele burden might thus be associated with increased 'net RAS activity' in tissue systems. Any phenotype critically-regulated by tissue RAS may be more prominent within a population amongst those of DD genotype if tissue ACE levels are the rate limiting step in the tissue RAS. Many physiological stimuli cause induction of RAS (including ACE) gene expression. Prospective studies of polymorphism influence on the phenotypic response to a physiological challenge therefore allow not only elucidation of a role for tissue RAS in the control of that phenotype, but also examination of the molecular control of tissue ACE expression. For instance, if the D allele is associated with more responsive gene transcription, any given physiological challenge will cause a disproportionate change in RAS-dependent phenotype in association with the D allele.

The present invention is not restricted to administration of active agents to individuals of a particular genotype. However, it is evident that the benefits of the invention may be seen in circumstances where there may be elevated levels of, say, ACE. This lends support to the invention. A study was conducted, in which various parameters were measured, at the start and end of a 10 week physical training period in male Caucasian military recruits. A possible influence of ACE genotype on systolic blood pressure is seen in the cohort as a whole, i.e. amongst the individuals who completed training. This trend is not statistically significant prior to training (p for heterogeneity=0.35), but approaches significance at the end of training (p for heterogeneity=0.07) when systolic blood pressure for those of II genotype was significantly lower than those of DD genotype (122.7±1.4 vs. 118.0±1.5 mmHg: p<0.05). Diastolic blood pressures did not differ before or after basic training between those of different genotype (pre-training 70.3±1.37 vs. 70.6±0.8 vs. 69.4±1.3 mmHg, p=0.75: post-training 69.7±1.23 vs. 70.1±0.81 vs. 69.9±1.23 mmHg, p=0.96: for II, ID and DD respectively).

In another study, the upper limb performance of army recruits was observed, since they are specifically trained for power during army basic training. Tests were conducted at selected timepoints, i.e. the start of training, mid-training (5 weeks), and end-training (10 weeks).

For paired data on calf strength, there was a suggestion of a genotype effect. Mean of paired percentage changes were 7.6±14.1 vs. −6.4±4.1: p=0.19.

At the start of training, there were no differences in biceps power (109.4 N±8.5 vs. 111.5 N±5.6 for II vs. D-allele: p=0.86). However, at the end of training, there had been a significant improvement in both groups, but to a much greater degree amongst those of II genotype (198.7±26.1 vs. 141±9.37 for II vs. D-allele: p-3.01). The mean percentage change was 77.0±24.4% vs. 23.7±6.2% for II vs. D-allele respectively: p=0.003). Mean changes for those of II genotype were 109.4 vs. 198.7, compared to 109.8 vs. 144.9 for those of ID genotype, and 116.4 vs. 125.9 for those of DD genotype: II<ID, and II<DD with p<0.05 at end of training). The data are in duration of exercise (seconds).

Data for press-ups were similar at start of training (mean 51.2±4.0 vs. 50.4±2.4 vs. 47.5±4.3: n=29, 69 and 22: for II, ID and DD respectively: p>0.05 for all comparisons. At the end of training, the figures were 61.9±4.2 vs. 59.5±3.6 vs. 45.0±6.2: n=19, 44 and 12: for II, ID and DD respectively: p<0.05 for II vs. DD and ID vs. 20DD).

The change in VO$_2$max (from a baseline level similar across genotypes) was +0.055±0.037 vs. −0.003±0.021 vs. −0.068±0.052: p<0.05 for II vs. DD). [V0$_2$max is the maximal oxygen consumption (in ml) per unit time (min.)]

Weight increased significantly more for those of II genotype than those with a D allele (by 2.9±0.8% vs. −0.1±0.6%: n=20 vs. 61: p=0.01: p<0.05 for II vs. ID). This is a balance of changes in fat and muscle, both of which might be differentially regulated by the ACE genotype.

Percentage body fat was similar at the outset (8.6±0.7% vs. 9.3±0.3%: n=29 vs. 93 for II vs. D allele: p=0.33). However, this changed by a fraction of 0.20±0.09 vs. 0.007±0.003: n=20 vs. 58: p=0.02, i.e. II fractional fat content increased by about 20% vs. less than 1% for those with a D allele.

Those with a D allele had a slightly lower lean body mass at outset (64.6±1.2 vs. 62.5±0.67: n=29 vs. 93: p=0.12), but this gap widened after training (65.9±1.3 vs. 62.6±0.82: n=19 vs. 57: p=0.046).

Fat mass was similar at outset (6.18 kg±0.54 vs. 6.49 kg±0.26: n=29 vs. 93: p=0.57). Change in fat weight was genotype-dependent (0.73 kg±0.39 vs. −0.26 kg±0.20: n=19 vs. 57: p=0.02), i.e. mean of percentage changes in body fat mass were an increase of 23% for those of II genotype vs. a change of just 1% amongst those with a D allele.

In another study, 33 elite unrelated male British mountaineers with a history of ascents beyond 7000 m without the use of supplemental inspired oxygen were identified by the British Mountaineering Council. DNA was extracted from a mouthwash sample of the 25 male respondents, and ACE genotype determined using a three-primer polymerase chain reaction (PCR) amplification (51). Genotype distribution was compared to that of 1906 British males free from clinical cardiovascular disease (52). Mean (SD) age was 40.6 (6.5) years in the 25 subjects, and 55.6 (3.2) years amongst the 1906 controls. Both groups were in Hardy Weinberg Equilibrium. Both genotype distribution and allele frequency differed significantly between climbers and controls (p 0.02 and 0.003 respectively), with a relative excess of II genotype and deficiency of DD genotype. Amongst the 15 climbers who had ascended beyond 8000 m without oxygen, none was of DD genotype [6 (40%) II and 9 (60%) ID: I allele frequency 0.65]. Further, ranked by number of ascents without oxygen, the top performer climbing over 8000 m was of II genotype (5 ascents, compared to a mean of 2.4+0.3 ascents for the >8000 m group, or 1.44+0.3 ascents for the climbers overall), as were the top two in this group for number of additional 7000 m ascents (>100 and 18, compared to a mean of 10.3+6.5 ascents).

Further, among athletes, an excess of the I allele is found amongst endurance runners, and an excess of the D allele amongst sprinters. Provisional data suggest that the D allele is found in excess in athletes in whose sport power (rather than endurance) plays an important role.

These data suggest that many aspects of human physical performance may be associated with the I allele, and thus with lower tissue ACE levels. Thus, total cardiac work is higher per unit of external work amongst those with two D alleles than those without, and ability to train to improve calf strength, biceps power, and press-ups were all associated with the I allele, with trainability being graded as II>ID>DD. These changes in performance may be partly related to changes in body composition, with a preservation of body mass and slight overall anabolic effect being associated with the I allele when compared to a lack of anabolism (or slight catabolic effect) being seen in those with a D allele. The marked changes in performance by genotype with more modest changes in muscle mass suggest that there is not only a genotype-associated effect on performance mediated through muscle bulk per se, but also an effect mediated through efficiency of muscle metabolism. This hypothesis is supported by the genotype-effect on energy stores in the form of fat.

Since the I allele is a surrogate marker for lower tissue ACE levels, it would seem likely that increased skeletal muscle performance, metabolic performance, limitation of catabolism, and promotion of anabolism may all be achieved by reducing tissue RAS activity pharmacologically. Both the inhibition of kinin degradation and antagonists to receptors for ATII might be expected to have such effects. The above data therefore suggest a metabolic role for human renin-angiotensin systems which has significant effects on the human as a whole.

In hindsight, although there are data in the prior art to support possible beneficial effects on muscle blood flow and glucose uptake in diseased states, there are no data to suggest any clinically or physiologically significant effects on whole body morphology, muscle or whole human physical performance, or on overall nutritive or morphological state. The data, however, do provide support and potential scientific rationale for the present invention.

These data suggest that endurance performance may indeed be improved by treatment with the specified agents. Pure power performance might also be improved, but possibly less effectively. The effects on mixed sport might depend very much on the relative contributions of power and endurance to success.

There might be a number of means through which the observed and anticipated effects might be mediated. These include:

(i) an increase in blood flow to tissues through vasodilation;

(ii) an increase in blood flow to tissues through angiogenesis (the growth of new vessels);

(iii) subsequent on (i), a fall in peripheral vascular resistance and an increase in cardiac output;

(iv) an increase in metabolic fuel (oxygen, fats, carbohydrates, and amino acids) uptake by tissues;

(v) an alteration in the balance of the fuel utilised (such as, for example, a shift towards the use of fatty acids from which more energy can be derived than from equivalent amounts of glucose);

(vi) an alteration in the supply of fuel from, for example, fat and liver stores;

(vii) a primary shift in both qualitative and quantitative substrate metabolism (such as lactate metabolism) and energy store release (such as fatty acid release) by metabolically active tissues including the liver;

(viii) a change in skeletal muscle cell type, reflected perhaps in a change in the relative numbers of type I and type II myocytes. This may be an important factor in the changes in performance which we are seeing.

(ix) a change in the numbers of mitochondria within cells;

(x) a change in the efficiency of metabolism within a cell or organism, reflected by the ability to perform more external, mechanical, or biochemical work for a reduced utilisation of oxygen or metabolic substrate or energy.

Other mechanisms may also apply.

The following Examples illustrate the invention and the evidence on which it is based, and also show how it may be put into effect in particular instances.

Example 1

This Example demonstrates that ACE inhibitors increase the mitochondrial membrane potential of cardiomyocytes. It is based on observation of the potential difference ($\Delta\Psi_m$) across the inner mitochondrial membrane that is generated by the extrusion of protons to the outside of the mitochondrion during the transport of electrons from electron-carrying coenzymes to molecular oxygen. Part of the energy stored in $\Delta\Psi_m$ is utilised to support the synthesis of most of the ATP derived from aerobic metabolism. Thus, $\Delta\Psi_m$ is an indicator of the energisation state of the mitochondrion, and also of the efficiency of oxygen utilisation to generate chemical energy. To investigate whether some of the therapeutic properties of ACE inhibitors could be accounted for by an increase in $\Delta\Psi_m$, this parameter was examined in rat cardiomyocytes, following pre-treatment with the ACE inhibitor lisinopril.

More particularly, cardiomyocytes were isolated from new-born Sprague-Dawley rats hearts and maintained in 30 mm tissue culture dishes in the presence of DMEM supplemented with 1% foetal calf serum at 37° C. in a humidified 5% $CO_2$ atmosphere. For experiments, cultures were treated with 1 µM lisinopril or with an equivalent amount of vehicle for various lengths of time, before analysis of $\Delta\Psi_m$.

To measure $\Delta\Psi_m$, the mitochondrial-specific probes rhodamine 123 (Rh123) and 5,5',6,6'-tetrachloro-1,1',3,3'-tetraethylbenzimidazolocarbocyanine iodide (JC-1) were used. Cells were incubated for 15 min with 2.5 µM Rh123 or for 10 min with 10 µl JC-1 (Molecular Probes) in fresh culture medium, at 37° C. and 5% $CO_2$. The cells were then washed twice with cold PBS, resuspended by trypsinisation and stored in the dark at 4° C. until the time of analysis (usually within 30 min). How cytometry was performed on a FACScan instrument. Data were acquired and analysed using Lysis II software (Becton Dickinson).

Results:

Cationic lipophilic fluorochromes such as Rh123 serve as reporter molecules to monitor mitochondrial activity. These dyes accumulate in the mitochondria' matrix in accordance with the Nernst equation. When used in combination with flow cytometry, they are effective probes to estimate changes of $\Delta\Psi_m$ in intact cells. As shown in FIG. 1, pre-treatment of cardiomyocytes with 1 µM lisinopril for 36 hours caused an increase in Rh123 fluorescence of about 30%, indicating that ACE inhibition induced an increase in $\Delta\Psi_m$.

Figure 2:
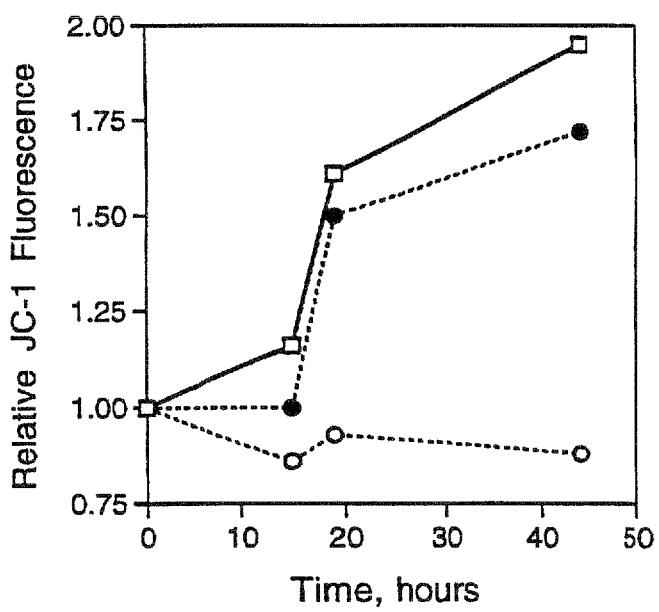
FIG. 2 shows that treatment of rat cardiomyocytes with 1 µM lisinopril for various lengths of time caused a progressive increase in red fluorescence (●) with a corresponding decrease in green fluorescence (o). Thus, the ratio of red to green fluorescence (□) increased as the time of incubation with lisinopril progressed.

JC-1 is a more reliable and sensitive fluorescent probe for assessing changes in $\Delta\Psi_m$. At low concentrations, JC-1 exists mainly in a monomeric form which is characterised by the emission of green fluorescence. Upon accumulation in the mitochondrial matrix JC-1 forms J-aggregates in proportion to the magnitude of $\Delta\Psi_m$. These aggregates are characterized by the emission of red fluorescence. Thus, an increase in the red to green fluorescence ratio indicates an increase in $\Delta\Psi_m$. FIG. 2 shows that treatment of rat cardiomyocytes with 1 µM lisinopril for various lengths of time caused a progressive increase in red fluorescence (●) with a corresponding decrease in green fluorescence (o). Thus, the ratio of red to green fluorescence (□) increased as the time of incubation with lisinopril progressed.

These experiments demonstrate that treatment with ACE inhibitors increases $\Delta\Psi_m$. This indicates that ACE inhibitors may protect against ischaemic situations and/or improve mechanical/biosynthetic performance by increasing the efficiency of energy transduction in the mitochondrion.

Example 2

Ninety military recruits were studied before and after military training of 12 weeks duration. These were randomised to receive the AT1-receptor antagonist Losartan or placebo.

There was a consistent trend for the recruits to improve their VO2 max at anaerobic threshold, although a distinction was observed, according to genotype. The results shows a gain of 2.1±6.8 ml/min for II genotype on placebo vs. −1.1±6.5 ml/min for DD genotype on placebo, and a gain of 0.3±6.3 ml/min for II on losartan vs. −1.8±6.3 ml/min for DD on Losartan. When combined, the difference in gain was 1.3±6.6 ml/min for II on vs. −1.4±6.4 ml/min for DD: p 0.07).

The data for VO2 max showed a similar trend, as did measures of muscle fatigue. These data are consistent with an enhanced ability, especially for those of II genotype (and thus lower ACE activity) to achieve higher workloads, before reaching anaerobic threshold, and therefore to be more resistant to fatigue in situations of moderate to intense exercise.

Example 3

The bioactive element of the resin angiotensin system (RAS) is angiotensin II (AT II). Elevations of AT II in plasma or in local tissue would indicate conditions in which inhibition of the RAS may have significant therapeutic benefit even where partial inhibition of the RAS has been achieved (such as by therapy with ACE inhibitors).

ATT II was measured as follows: Blood samples were collected after supine rest of at least 10 minutes. An antecubital polyethylene catheter was inserted and 10 ml of venous blood were drawn. After immediate centrifugation, aliquots (EDTA plasma sample) were stored at −70° C. until analysis. Angiotensin II was measured using a commercially available radioimmunoassay (IBL, Hamburg, Germany, sensitivity 1.5 pg/ml). After extraction of the plasma samples, AT II is assayed by a competitive radioimmunoassay. This radioimmunoassay is using a rabbit anti-AT II antiserum and a radio-iodinated AT II tracer. Bound and free phases are separated by a second antibody bound to solid phase particles, followed by a centrifugation step. The radioactivity in the bound fractions is measured and a typical standard curve can be generated. The test has a cross-reactivity with AT 1 of <0.1% and a within and between run reproducibility between 3.9 and 8.6%. The reference range for healthy subjects is 20 to 40 pg/ml.

Figure 3:
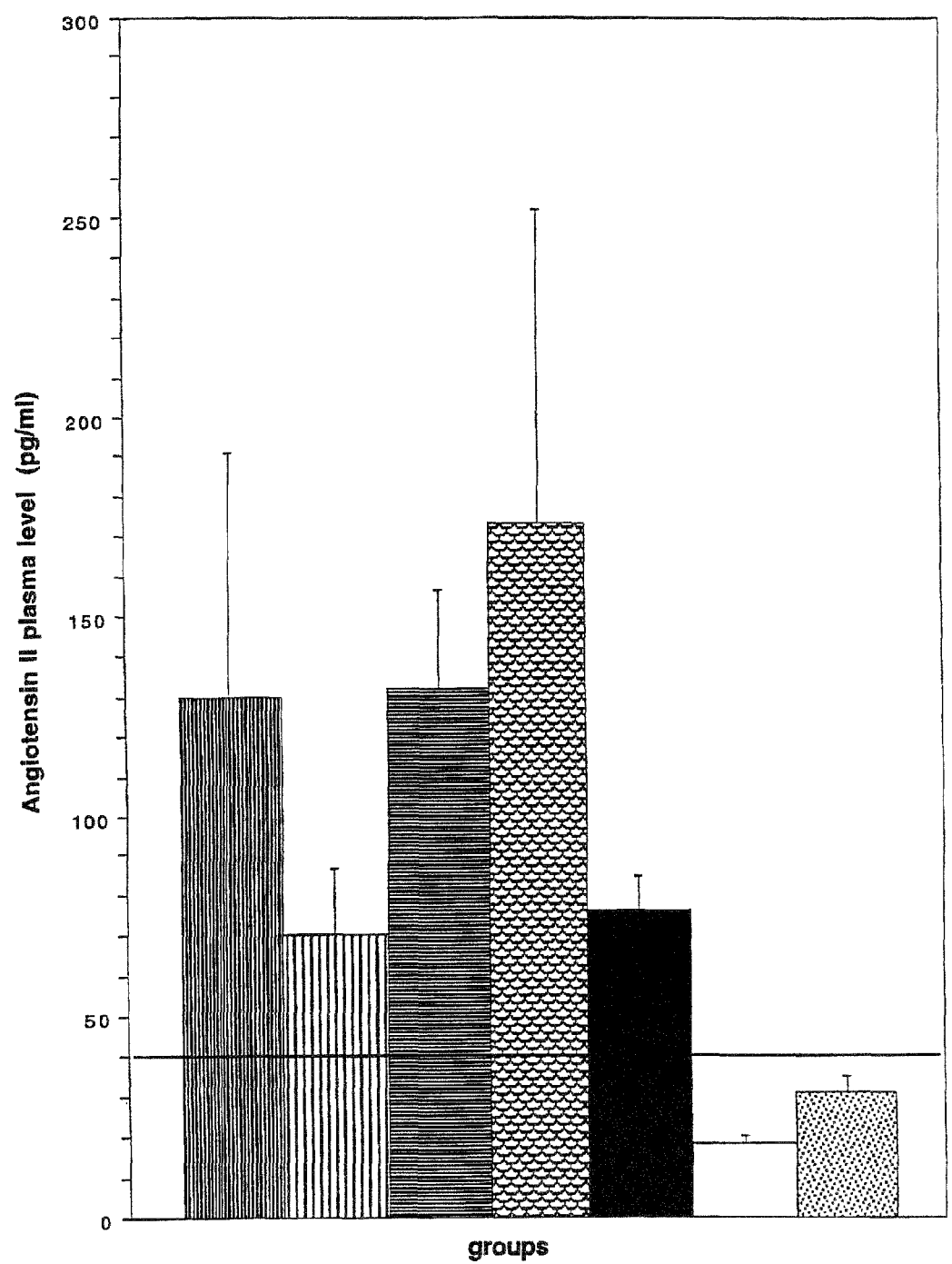
FIG. 3 shows angiotensin II plasma levels for a variety of cachectic conditions.

A variety of cachectic conditions, for instance due to chronic heart failure, AIDS, liver cirrhosis, and cancer has been studied. Results are presented in FIG. 3, where the bars (from left to right) relate to AIDS cachexia (n=6), cancer cachexia (n=7), cardiac cachexia (n=17), idiopathic cachexia (n=2), liver cirrhosis cachexia (n=6), malnutrition (n=6) and non-cachectic heart failure (n=11).

Activation of the RAS has been found, in the cachectic conditions, as evidenced by elevated plasma AT II levels (mean AT II plasma levels were clearly above the upper limit of the normal range of 20 to 40 pg/ml). This is not dependent on any specific actiology for the cachectic disorder; in fact, elevated AT II plasma levels (i.e. RAS activity) are also found in cases of idiopathic cachexia, i.e. cachexia of unknown origin. Nevertheless, activation of the RAS is apparently specific for cachectic disorders, as it is not seen in patients with a similar degree of weight loss consequent upon malnutrition.

Example 4

Experiments were conducted, to demonstrate that the blockade of the RAS is of benefit for cachectic patients, even if previously treated with an ACE inhibitor. Patient 1 had cachexia due to chronic heart failure (CHF) (age 74 years, male, weight 50.0 kg, height 178 cm, previous weight loss 15.3 kg in 3 years=chronic weight loss). Patient 2 had CHF and a muscle myopathy suffering from idiopathic cachexia (age 38 years, male, weight 62 kg, height 180 cm, previous weight loss 11 kg in year=recent weight loss). Each was treated with Losartan (50 mg once daily). Clinical status and parameters of body composition, strength and treadmill exercise capacity were studies, at baseline and during follow-up. Both patients had evidence of CHF with impaired exercise capacity and impaired left ventricular function (LVEF<40%). Both patients had a good compliance.

Bioelectrical impedance analysis (patient 1 and 2) was performed in the erect position using a body fat analyser (TANITA TBF-305, Tanita Corporation, Illinois, USA). Lean and fat mass were automatically analysed based on equations supplied and programmed into the machine by the manufacturer. These equations are based upon a comparison with measurements in a health population.

Dual energy X-ray absorptiometry (DEXA) (patient 1): Whole body DEXA-scans were performed using a Lunar model DPXIQ total body scanner (Lunar Radiation Company, Madison, Wisc., USA, Lunar system software version 4.3c). The subject was at each time point scanned rectilinearly from head to toe. A scan takes less than 20 min. The mean radiation dose per scan is reported to be about 0.75 μSv (53), about 1/50th of a normal chest X-ray. The DEXA method can be used to obtain from body density analyses values of fat tissue mass, lean tissue mass. The technical details of DEXA, performance and segment demarcation have been described (54,55). The error of lean tissue measurements is >2% and of fat tissue measurements <5% (56).

Treadmill exercise test (Patients 1 and 2): The patients underwent symptom limited treadmill exercise testing. A standard Bruce protocol with the addition of a "stage 0" consisting of 3 min at a speed of 1 mile per hour with a 5% gradient was used. The patients breathed through a one-way valve connected to a respiratory mass spectrometer (Amis 2000, Odense, Denmark) and minute ventilation, oxygen consumption and carbon dioxide production were calculated on line every 10 seconds using a standard inert gas dilution technique. Patients were encouraged to exercise to exhaustion. Exercise time and oxygen consumption at peak exercise adjusted for total body weight (peak $VO_2$ in ml/kg/min) were measured as an index of the exercise capacity.

Assessment of quadriceps muscle strength (Patients 1 and 2): The subjects were seated in a rigid frame, with the legs hanging freely. An inelastic strap attached the ankle to a pressure transducer. The recording (Multitrace 2, §, Jersey, Channel Islands) from the pressure transducer was used to assess strength and to provide visual feedback to the subject. A plateau of maximum force production indicated that the contraction was maximal. The best of three voluntary contractions on each leg, with a rest period of at least one minute in-between, was taken to represent the maximal voluntary quadriceps muscle strength of the right and left leg, respectively.

Results include a follow-up of 126 days for patient 1 and 83 days for patient 2. Both patients were also studied at intermediate time points. Both patients improved during treatment by 1 NYHA symptom class. In both patients, the exercise capacity improved during the study (exercise time: patient 1 and 2, peak $VO_2$: patient 2). There was evidence that in both patients, quadriceps muscle strength improved in both legs. These clinical benefits were achieved against the background of a weight gain of 4.6 kg in patient 1 (lean and fat tissue gain), and by stopping the process of weight loss and apparently improving the general clinical status and relative muscle performance, i.e. muscle quality (patient 2). No side-effects of treatment were observed.

Example 5

The SOLVD treatment study (57) was a randomized, double-blind, and placebo-controlled trial investigating the effects of enaiapril treatment in clinically stable patients with a LVEF of 35% or less and evidence of overt congestive heart failure. The precis e details of study organisation, inclusion criteria, run-in period (2 to 7 days) and stabilization period (14 to 17 days), randomisation, treatment titration and follow-up have been reported previously (57). Based also on data not otherwise available, the results have been re-analysed, restricted to subjects who participated in the SOLVD treatment trial, who had been free of edema at baseline, who had survived for at least 4 months thereafter, who had weight measurements at baseline and from at least one follow-up visit at 4 months or later. The baseline clinical characteristics of these 2082 patients were not significantly different from the characteristics of the total study population.

Of the 2082 patients, 1055 patients were randomised to treatment with enalapril (2.5 to 20 mg per pay) and 1027 patients to treatment with placebo. Body weight at baseline and during follow-up were measured per protocol. Body height was not recorded.

Comparison of means between groups was carried out using an unpaired t-test. Comparison of proportions between groups was made by employing the chi-square test. With regards to the definition of the presence of cachexia different, a priori suggested, cut-points (58) of 5.0%, 7.5%, 10.0% and 15.0% weight loss were considered. To address the question of whether or not ACE inhibitors influence the risk of first occurence of cachexia, the cumulative incidence of cachexia in the two treatment groups was plotted, and analysed employing the log-rank statistic (59). In the analysis of first occurence of cardiac cachexia, at any given follow-up visit, absence of information on cardiac cachexia (i.e. weight not documented at this visit) is treated as censored. The effect of cardiac cachexia on survival is assessed using Cox proportional hazard analysis (58). For these analyses, cardiac cachexia is treated as a time-dependent covariate. The assessment of cardiac cachexia at 4, 8, and 12 months was used in the analysis. These are the time points in the follow-up period with relatively high proportion of complete information on cachexia status.

The primary analysis was intention-to-treat. Statistical significance is claimed at a computed p-value <0.05 (two-sided testing). Estimates of effects are provided along with their 95% confidence intervals. Results are adjusted for a priori identified prognostic factors such as age, gender, NYHA functional class, LVEF (up to or more than 25%), and treatment status (enalapril vs placebo, in the case of assessing the effect of cardiac cachexia on survival).

Of the 2082 CHF patients in this study, 657 (31.6%) developed up to 7.5% weight loss during follow-up. The cumulative frequency of cardiac cachexia increased continuously over time. The frequency of ≥7.5% weight loss (cross-sectional) at 1 year was 8.5% and it increased to 15.5% (2 years), and 17.2% (3 years). At baseline, patients who developed cardiac cachexia with ≥7.5% weight loss during follow-up were 1.3 years older (mean 61.2 vs 59.9, p<0.01), had 2.7 kg higher weight (mean 80.5 vs 77.8 kg, p<0.001), and they were slightly more frequently treated with diuretics (87.2 vs 82.6%, p<0.01). Of the patients in this study, 375 (18.0%) were female. Female CHF patients developed cardiac cachexia more frequently (39.5% vs 29.8% in males for ≥7.5% weight loss, p<0.001). Otherwise the baseline clinical characteristics, particularly with regards to NYHA class, LVEF, and disease etiology, of patients who developed cardiac cachexia and those who did not were similar. The following clinical characteristics at baseline were independently related to the subsequent development of cardiac cachexia: age (RR, p<0.001), NYHA class, LVEF, and treatment.

The development of cardiac cachexia was closely related to subsequently impaired survival. All a priori identified competitive cut-points for cardiac cachexia were related to impaired survival, independent of the effects of age, gender, NYHA class, LVEF, and treatment allocation. Of the 756 deaths observed during follow-up, 223 occurred in patients who had been classified as cachectic (≥7.5% weight loss) at the last visit prior to death, i.e. 29.5% of deaths in CHF patients occurred with cardiac cachexia being present. Amongst different cut-offs for cardiac cachexia between 5 and 15%, weight loss 6.5% was the strongest predictor of impaired mortality. The crude effect of cachexia (weight loss ≥6.5%) on survival was highly significant: RR 1.47 (95% confidence interval: 1.27 to 1.70), $p^{-1}={}^{-}0.00000017$.

Patients who were allocated to treatment with enalapril had a significantly lower risk of developing cardiac cachexia during follow-up. The crude effect of treatment allocation with enalapril was significantly related to a reduced risk of developing cardiac cachexia: RR 0.81 (95% confidence interval: 0.70 to 0.95), p=0.0085. Treatment allocation to enalapril had a significantly beneficial effect on survival independently of the effect of age, gender, NYHA class, and LVEF also in this subset of patients of the SOLVD treatment trial (p<0.01). When adjusted also for the presence of cardiac cachexia (6.5% weight loss) at 4 or 8 months, the treatment effect remained significant. In patients who developed weight loss of at least 7.5% at any time point, only 10 patients with subsequently recorded weights equal to or higher than the baseline weight were found (enalapril group: 6, placebo: 4).

This demonstrates that significant weight loss, i.e. cardiac cachexia, is a frequent event in CHF patients. Weight loss≥7.5% occurs in about ⅓ of patients over 3 years. Spontaneous reversal of the weight loss is a very rare event occurring in less than 2% of cases. Cardiac cachexia is closely and independently linked to impaired survival of CHF patients. Treatment with an ACE inhibitor, enalapril, in addition to conventional therapy, reduced the frequency of the risk of death and the risk of developing cardiac cachexia. Overall, enalapril therapy reduced the risk of developing cardiac cachexia by 19%.

REFERENCES

1. Kern & Brown, N. Eng. J. Med 323(16) 1136-1137 (1990)
2. Yamada et al, *Circ. Res.* 68 141-149 (1991)
3. Campbell et al, *J. Clin. Invest.* 78 31-39 (1986)
4. Ohkubo et al, *J. Biol. Chem.* 261 319-323 (1986)
5. Naftilan et al, *J. Clin. Invest.* 87 1300-1311 (1991)
6. Gunther et al, *J. Cell. Biol.* 92 289-298 (1982)
7. Dzau, *Circulation* 77 (Suppl. 1)1-1-1-3 (1988)
8. Dzau, *Circulation* 77 (Suppl. I) 1-4-1-13 (1988)
9. Campbell, *J. Cardiovasc. Pharmacy!.* 10(Suppl. 7) S1-S8 (1987)
10. Campbell, *J. Clin. Invest.* 79:1 (1987)
11. Admiraal et al, *Hypertension* 15 44-55 (1990)
12. Lilly et al, *Circ. Res.* 57(2) 312-318 (1985)
13. Swales et al, *Clin. Exp. Hypertens. A* 5(7-8) 1127-1136 (1983)
14. Iwai & inagami, *J. Hypertens.* 10 717-724 (1992)
15. Ferrario et al, *Hypertension* 18(5 Suppl.) 111:126-133 (1991)
16. Dzau, *J. Hypertens.* 7 933-936 (1989)
17. Sibony et al, *Hypertension* 21 827-835 (1993)
18. Yosipov et al, *Hypertension* 23 369-374 (1994)
19. Re et al, *Biochem. Biophys. Res. Comm.* 119 220-225 (1984)
20. Eggena et al, *Hypertension* 22(4) 496-501 (1993)
21. Brink et al, *J. Clin. Invest.* 97(11) 2509-2516 (1996)
22. Tamura et al, *Am. J. Physiol.* 272(2) R1704-1711 (1997)
23. Shimizu et al, *Clin. Exp. Pharmacy!. Physiol.* 20(5) 369-372 (1993)
24. Jacob et al, *Metabolism* 45(5) 535-541 (1996)
25. Henriksen et al, *Diabetes* 45 (Suppl. 1) S125-S128 (1996)
26. Hoenack & Roesen, *Diabetes* 45 (Suppl. 1) S82-S87 (1996)
27. Rattigan et al, *Am. J. Physiol.* 271 (1 Pt. 1) E96-E103 (1996)
28. Sabbah et al, *Am. J. Physiol.* 270 (1 Pt. 2) H115-H120 (1996)
29. Schieffer et al, *Am. J. Physiol.* 269(2) H1507-H1513 (1995)
30. Henriksen & Jacob, *Metabolism* 44(2) 267-272 (1995)
31. Dragovic et al, *Diabetes* 45 (Suppl. I) S34-S37 (1996)
32. Vaghy et al, *Peptides* 16 (8) 1367-1373 (1995)
33. Zhang et al, *Circulation* 95(1) 14-16 (1997)

34. Seyedi et al, *Hypertension* 26(1) 164-170 (1995)
35. Coats, *Cardiology* 87 (Suppl. 1) 11-15 (1996)
36. Munzel et al, *Herz* 18 (Suppl. 1) 400-405 (1993)
37. Dietze et al, *Diabetes* 45 (Suppl. 1) S110-S114 (1996)
38. Moan et al, *J. Hum. Hypertension* 9 (Suppl. 5) S45-S50 (1995)
39. Broqvist et al, *Eur. Heart J.* 13(9) 1217-1224 (1992)
40. Predel et al, *J. Cardiovasc. Pharmacol.* 23 (Suppl. 1) S25-28 (1994)
41. Lievre et al, *Hypertension* 25 92-97 (1995)
42. Cambien et al, *Am. J. Hum. Genet.* 43 774-780 (1988)
43. Mattu et al, *Circulation* 91 270-274 (1995)
44. Rigat et al, *J. Clin. Invest.* 86 1343-1346 (1990)
45. Rigat et al, *Nuc. Acids. Res.* 20(6) 1433 (1992)
46. Tiret et al, *Am. J. Hum. Gen.* 51 197-205 (1992)
47. Costerousse et al, *Biochem. J.* 290 33-40 (1993)
48. Pinto et al, *Circulation* 90 (4 Pt. 2) 1-36 (1994)
49. Danser et al, *Circulation* 92(6) 1387-1388 (1995)
50. Harrap et al, *Hypertension* 21 455-460 (1993)
51. Montgomery et al, *Circulation* 96 741-747 (1997)
52. Miller et al, *Thrombosis Haemost.* 75 767-771 (1996)
53. Fuller et al, *Clinical Physiology* 12 253-266 (1992)
54. Mazess et al, *Calc7f. Tissue Mt.* 44 228-232 (1989)
55. Mazess et al, *Am. J. Clin. Nuts.* 51 1106-1112 (1990)
56. Ley et al, *Am. J. Clin. Nutr.* 55 950-954 (1992)
57. The SOLVD Investigators, *N Engl. 1 Med* 325 293-302 (1991)
58. Cox, *J. Royal Statistical Society* N34 187-220 (1972)
59. Kalbfleisch & Prentice, "The Statistical Analysis of Failure Time Data", New York: John Wiley and Sons Inc. (1980)

We claim:

1. A method for the treatment of a person, wherein said method comprises administering to a person with hypertension and left ventricular hypertrophy in need of such treatment an inhibitor of the renin-angiotensin system wherein the inhibitor is an $AT_I$ receptor antagonist and wherein said antagonist consists of losartan in an amount effective to reduce the risk of stroke in patients with hypertension and left ventricular hypertrophy.

* * * * *